(12) United States Patent
Soppimath et al.

(10) Patent No.: US 10,722,454 B1
(45) Date of Patent: *Jul. 28, 2020

(54) SUCCINYLCHOLINE PREFILLED SYRINGE, COMPOSITIONS AND METHODS

(71) Applicant: Nevakar Inc., Bridgewater, NJ (US)

(72) Inventors: Kumaresh Soppimath, Skillman, NJ (US); Prem Sagar Akasapu, Edison, NJ (US)

(73) Assignee: NEVAKAR INC., Bridgewater, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/836,483

(22) Filed: Mar. 31, 2020

Related U.S. Application Data

(62) Division of application No. 16/272,815, filed on Feb. 11, 2019.

(60) Provisional application No. 62/642,326, filed on Aug. 13, 2018.

(51) Int. Cl.
| | |
|---|---|
| *A61K 9/00* | (2006.01) |
| *A61M 5/145* | (2006.01) |
| *A61K 47/02* | (2006.01) |
| *A61M 25/00* | (2006.01) |
| *A61K 31/137* | (2006.01) |
| *A61M 5/31* | (2006.01) |
| *A61K 47/12* | (2006.01) |
| *A61M 5/178* | (2006.01) |
| *A61M 39/10* | (2006.01) |
| *A61K 31/225* | (2006.01) |

(52) U.S. Cl.
CPC .......... *A61K 9/0019* (2013.01); *A61K 31/137* (2013.01); *A61K 31/225* (2013.01); *A61K 47/02* (2013.01); *A61K 47/12* (2013.01); *A61M 5/1452* (2013.01); *A61M 5/178* (2013.01); *A61M 5/3129* (2013.01); *A61M 25/0097* (2013.01); *A61M 39/10* (2013.01)

(58) Field of Classification Search
CPC ....... A61M 5/178; A61M 39/10; A61K 47/02; A61K 47/12; A61K 31/137
See application file for complete search history.

(56) References Cited

U.S. PATENT DOCUMENTS

2011/0130717 A1* 6/2011 David ................... A61M 39/10
  604/68
2019/0201630 A1* 7/2019 Vogt .................... A61M 5/3158

* cited by examiner

*Primary Examiner* — Rebecca E Eisenberg
*Assistant Examiner* — Anh Bui
(74) *Attorney, Agent, or Firm* — Umberg Zipser LLP

(57) ABSTRACT

Pre-filled syringes, pharmaceutical compositions, and kits and methods relating to same allow for emergency administration of one or more drugs from prefilled glass syringes to a patient via a needleless connector. In preferred embodiments, the prefilled glass syringe has a drug volume of at least 5 mL, has a Luer-lock, and has a syringe tip with an internal channel that has a diameter of about 1.7 mm. Such syringes advantageously allow storage of emergency drugs without leaching of plastic materials and degradation, and substantially improve the safety profile where the syringe is attached to an IV line via a needleless connector.

19 Claims, 4 Drawing Sheets

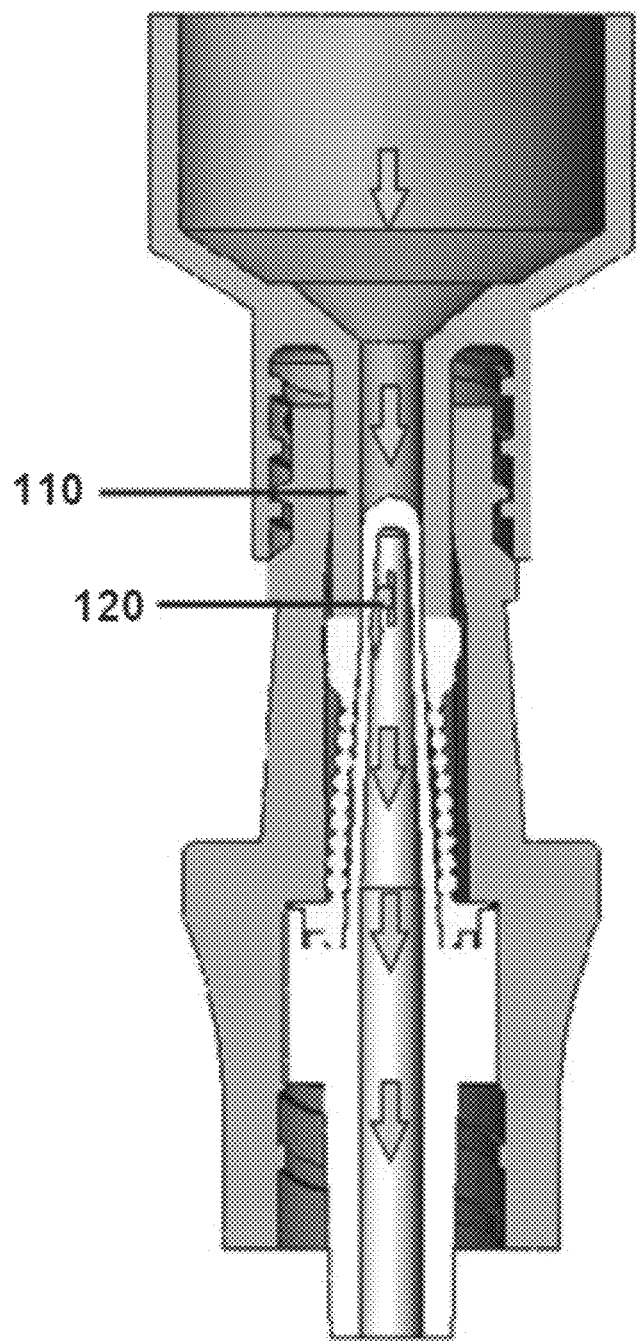
Prior Art Fig.1

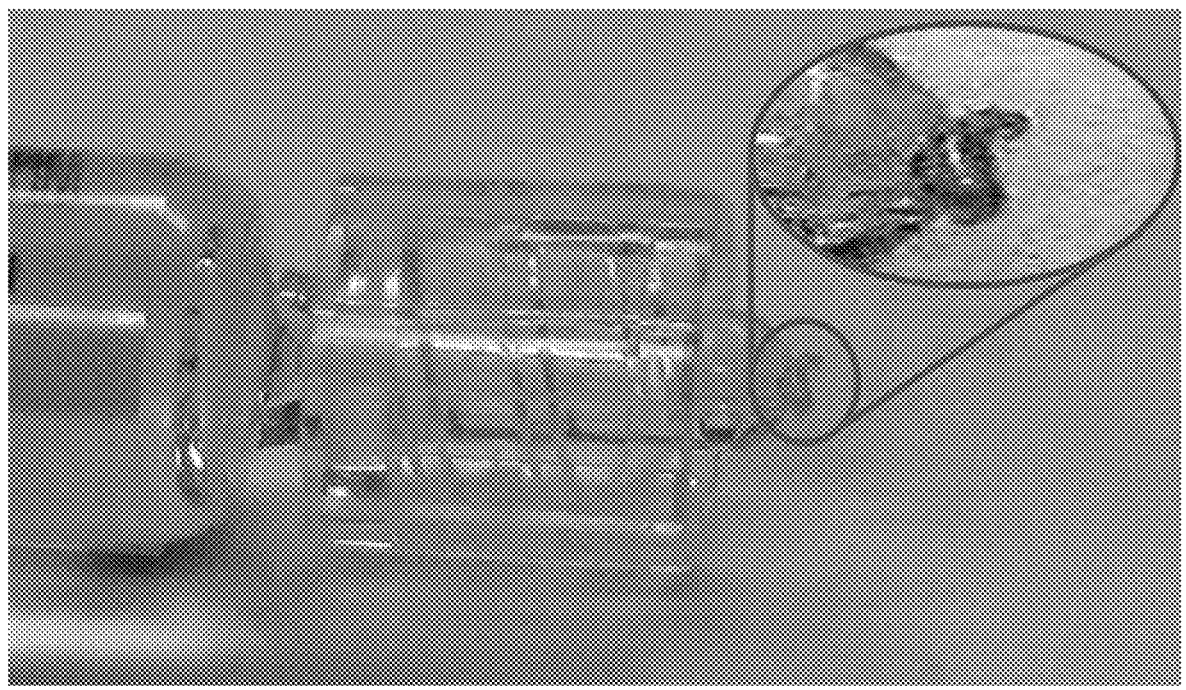
Prior Art Fig. 2A
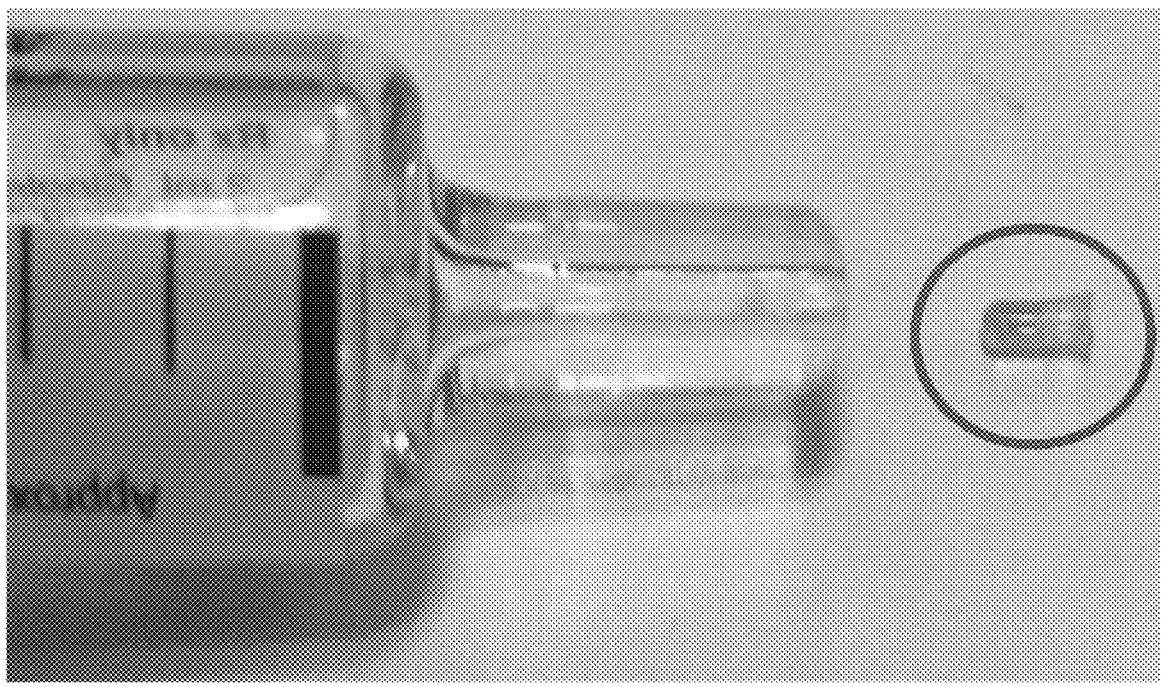
Prior Art Fig. 2B

SUCCINYLCHOLINE PREFILLED SYRINGE, COMPOSITIONS AND METHODS

This application claims priority to allowed US patent application with the Ser. No. 16/272,815, which was filed Feb. 11, 2019, which claims priority to US provisional patent application with the Ser. No. 62/642,326, which was filed Mar. 13, 2018, the contents of which are herein incorporated by reference.

FIELD OF THE INVENTION

The present disclosure relates to kits, prefilled syringes, pharmaceutical compositions and methods of use thereof, particularly as it relates to prefilled glass syringes containing emergency medication for administration through needleless connectors.

BACKGROUND OF THE INVENTION

The background description includes information that may be useful in understanding the present disclosure. It is not an admission that any of the information provided herein is prior art or relevant to the presently claimed invention, or that any publication specifically or implicitly referenced is prior art.

All publications and patent applications herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

Needleless devices for connecting intravenous (IV) catheters, administration sets, and syringes have been developed over the last decades and helped significantly reduce needlestick injuries among health care providers. Unfortunately, the use of needleless connectors has also been associated with an increase in various complications such as catheter-related bloodstream infection and catheter lumen occlusion. To circumvent at least some of these problems, various improvements have been implemented. For example, several simple needleless connectors use a split septum and/or other non-moving parts to avoid backflow of blood into the IV line while still allowing needleless access to the IV line. More complex needleless connectors employ internal moving components such as unidirectional valves to control the flow of fluids within the connector. While simple connectors advantageously provide simplicity of use and manufacture, negative fluid displacement or reflux will often occur upon withdrawal of the cannula due to their relatively large size. On the other hand, connectors with mechanical valves are more complex and therefore less simple in manufacture, but typically have no or only minor reflux.

A representative complex needleless connector is shown in Prior Art FIG. 1, in which a syringe with a male luer tip 110 is coupled to a needleless connector with a reversed internal blunt cannula 120. Exemplary complex needleless connectors are described, for example, in U.S. Pat. Nos. 9,205,243 and 9,750,926, and such and similar connectors may further include a sealing member and regulator acting as a second valve as is described, for example, in US Publication Nos. 20180099137 and 20190001114. While such and other complex needleless connectors eliminate the risk of needlestick injuries and at least conceptually simplify operation, catheter related blood stream infections have become more prevalent.

Worse yet, and particularly in emergency settings where certain drugs (e.g., adenosine, amiodarone, succinylcholine, etc.) need to be administered without delay and interruption, complex needleless connectors can contribute to catastrophic failure. In a Drug Safety Communication, the FDA had more recently indicated that pre-filled glass syringes can become clogged and malfunction during the process of connecting them to pin-activated needleless IV access systems (see Prior Art FIGS. 2A and 2B). Unfortunately, such failure is not detected until after the syringe is inserted into the pin-activated needleless i.v. access system. For example, the action of inserting the syringe can cause the pin in the access system to clog or break off in the syringe tip, thus preventing delivery of the medication and necessitating placement of a new i.v. access line. As a consequence, the FDA advised that the use of needleless pre-filled glass syringes in emergency situations should be avoided, if possible (see URL: www.fda.gov/Drugs/DrugSafety/ucm254215.htm). Moreover, because of recent adverse glass syringe connection events, the FDA has recognized that demonstrating conformity to the ISO 11040-4 standard alone does not ensure that the glass syringes can be properly connected to connecting devices. Therefore, sponsors who seek to rely on conformity to the ISO 11040-4 standard in submissions for glass syringe products should also submit information from supplemental tests to demonstrate that the glass syringe can be properly connected to connecting devices. Such safe connection has been elusive and challenging, particularly for prefilled glass syringes.

Thus, even though various methods of delivering emergency medication from syringes via needleless connectors are known in the art, all or almost all of them suffer from various disadvantages. Consequently, there is a need to provide improved devices, kits, and methods using glass syringes that improve safety and reliability of drug administration in emergency settings.

SUMMARY OF THE INVENTION

Various devices, compositions, kits, and methods are presented in which problems associated with emergency IV administration of various drug compositions via needleless connectors can be avoided. In especially preferred aspects, the emergency drug composition comprises succinylcholine that is contained in a prefilled glass syringe, and the syringe has a Luer-lock and a syringe tip with an internal channel that has a diameter of about 1.7 mm.

In one aspect of the inventive subject matter, the inventors contemplate a method for intravenously administering succinylcholine to a patient and/or providing skeletal muscle relaxation to a patient in need thereof that includes the steps of (a) providing a prefilled glass syringe containing a succinylcholine composition, wherein the succinylcholine composition comprises succinylcholine chloride, sodium chloride, and water, wherein the succinylcholine composition is substantially free of preservatives, and wherein the succinylcholine composition has a pH of about 3.0 to about 4.5, and wherein the syringe has a Luer-lock and a syringe tip with an internal channel that has a diameter of about 1.7 mm; (b) reversibly attaching the syringe to a patient's intravenous line via the Luer-lock; (c) delivering the succinylcholine composition from the syringe into the patient's intravenous line; and (d) administering the succinylcholine composition from the patient's intravenous line to the patient.

In some embodiments, the step of reversibly attaching the syringe to a patient's intravenous line comprises attaching the syringe to a needleless connector, which may include a reversed internal blunt cannula. Most typically, but not necessarily, the glass syringe has a volume of at least 5 mL.

In other embodiments, the succinylcholine composition has an osmolality of about 260 to about 340 mOsm/kg, and/or the succinylcholine chloride is present in the succinylcholine composition in an amount of about 20 mg/mL and the sodium chloride is present in the succinylcholine composition in an amount of about 6 mg/mL. It is further contemplated that the succinylcholine composition further comprises a pH adjusting agent (e.g., hydrochloric acid and/or sodium hydroxide), and/or that the pH of the succinylcholine composition is about 3.6.

With respect to the syringe it is contemplated that the syringe has a glide force of about 1 to about 20 N, and/or that the syringe has a break loose force of about 10 to about 30 N. In further embodiments, the syringe contains about 5 mL or about 10 mL of the succinylcholine composition, which may be administered to the patient at a rate of about 0.5 to about 10 mg per minute. Preferably, the succinylcholine composition in the glass syringe contains not more than about 6% total impurities after storage at 2-8° C. for 15 months as determined by HPLC. Viewed from a different perspective, the succinylcholine composition disposed in the glass syringe contains not more than about 4% succinylmonocholine chloride after storage at 2-8° C. for 15 months as determined by HPLC, and/or the succinylcholine composition disposed in the glass syringe contains not more than about 1% succinic acid after storage at 2-8° C. for 15 months as determined by HPLC.

In another aspect of the inventive subject matter, the inventors contemplate a kit that comprises a prefilled glass syringe containing a succinylcholine composition, wherein the succinylcholine composition comprises succinylcholine chloride, sodium chloride, and water, wherein the succinylcholine composition is substantially free of preservatives, and wherein the succinylcholine composition has a pH of about 3.0 to about 4.5. Preferably, the syringe has a Luer-lock and a syringe tip with an internal channel that has a diameter of about 1.7 mm.

Most typically, the glass syringe has a volume of at least 5 ml. Contemplated kits may further include an IV administration set with at least one needleless connector (e.g., needleless connector with a reversed internal blunt cannula).

With respect to contemplated succinylcholine compositions it is typically preferred that the succinylcholine composition has an osmolality of about 260 to about 340 mOsm/kg, and/or that the succinylcholine chloride is present in the succinylcholine composition in an amount of about 20 mg/mL and the sodium chloride is present in the succinylcholine composition in an amount of about 6 mg/mL. Moreover it is contemplated that the succinylcholine composition further comprises a pH adjusting agent (e.g., hydrochloric acid and/or sodium hydroxide) and that the pH of the succinylcholine composition is about 3.6. In some embodiments, the succinylcholine composition disposed in the glass syringe contains not more than about 6% total impurities after storage at 2-8° C. for 15 months as determined by HPLC, and in other embodiments the succinylcholine composition disposed in the glass syringe contains not more than about 4% succinylmonocholine chloride after storage at 2-8° C. for 15 months as determined by HPLC. In further embodiments, the succinylcholine composition disposed in the glass syringe contains not more than about 1% succinic acid after storage at 2-8° C. for 15 months as determined by HPLC.

Therefore, viewed from a different perspective, the inventors also contemplate a kit that comprises a prefilled glass syringe containing a drug for emergency medical administration, wherein the glass syringe has a volume of at least 5 ml, wherein the glass syringe has a luer-lock and a syringe tip with an internal channel that has a diameter of about 1.7 mm, and wherein the glass syringe and the drug are sterilized.

In particularly preferred aspects, the drug is succinylcholine, ephedrine, amiodarone, adenosine, epinephrine, atropine, methylprednisolone, metoprolol, diltiazem, or procainamide, and contemplated kits may further include an IV administration set with at least one needleless connector, and particularly a needleless connector with a reversed internal blunt cannula.

Viewed from yet another perspective, the inventors contemplate a prefilled glass syringe containing a drug composition for emergency medical administration of the drug through a needleless connector, wherein the glass syringe has a volume of at least 5 ml, wherein the glass syringe has a luer-lock, and wherein the glass syringe has a syringe tip with an internal channel that has a diameter of about 1.7 mm.

For example, suitable drug compositions include succinylcholine, ephedrine, amiodarone, adenosine, epinephrine, atropine, methylprednisolone, metoprolol, diltiazem, and procainamide. For example, the drug composition may comprise succinylcholine chloride, sodium chloride, and water, wherein the succinylcholine composition is substantially free of preservatives, and wherein the succinylcholine composition has a pH of about 3.0 to about 4.5.

Various objects, features, aspects, and advantages will become more apparent from the following detailed description of preferred embodiments, along with the accompanying drawing in which like numerals represent like components.

BRIEF DESCRIPTION OF THE DRAWING

Prior Art FIG. 1 depicts a cross sectional view of an exemplary known needleless connector with a reversed internal blunt cannula attached to a syringe with a male luer tip.

Prior Art FIG. 2A depicts a damaged/clogged syringe tip after disconnection from a needleless connector with a reversed internal blunt cannula, and Prior Art FIG. 2B depicts a glass syringe tip and broken off tip of a reversed internal blunt cannula of a needleless connector.

DETAILED DESCRIPTION

The inventors have now discovered that various emergency medications can be rapidly and safely administered through a needleless connector (that is typically fluidly coupled to an IV line into a patient) without the attendant risk of clogging or breakage that has been encountered in the past. More particularly, the inventors discovered that the likelihood of breakage can be significantly reduced by using a syringe having a widened inner diameter of a syringe tip. Advantageously, the inventors observed that such a widened inner diameter substantially increased the tolerance of the tip to angled insertion into a needleless connector and so dramatically decreased the likelihood of damaging static or moving internals of the needleless connector. Moreover, the inventors observed that such widening did not cause significant mechanical weakening of the syringe tip that could otherwise lead to chipping or breaking of the tip where a glass syringe is used.

Figure 3:
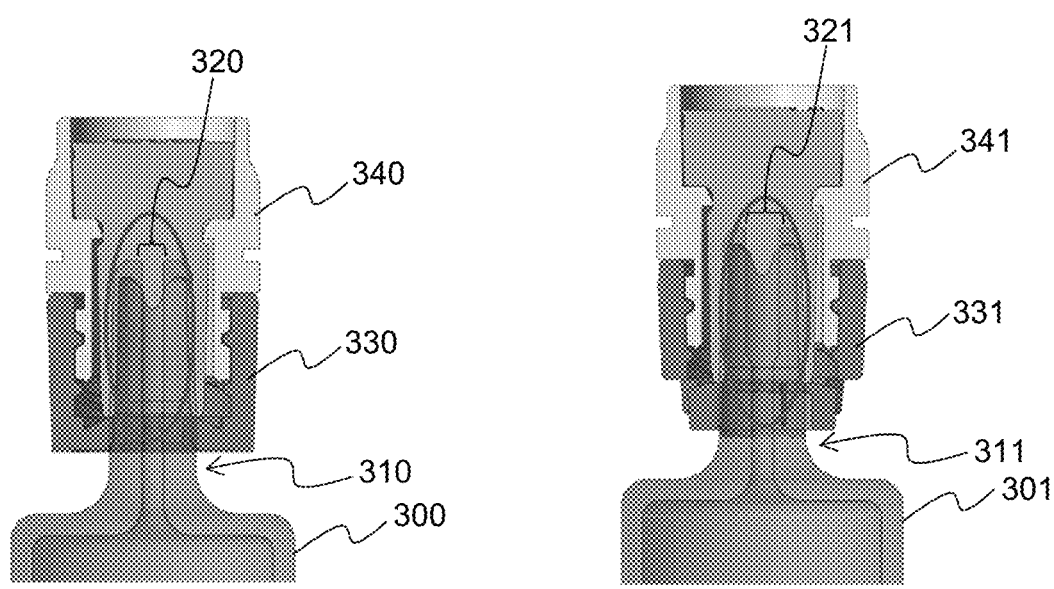
FIG. 3 depicts a comparison between a conventional attachment of a glass syringe to a needleless connector (left) and an attachment of a wide mouth glass syringe to a needleless connector (right) according to the inventive subject matter.
Figure 4:
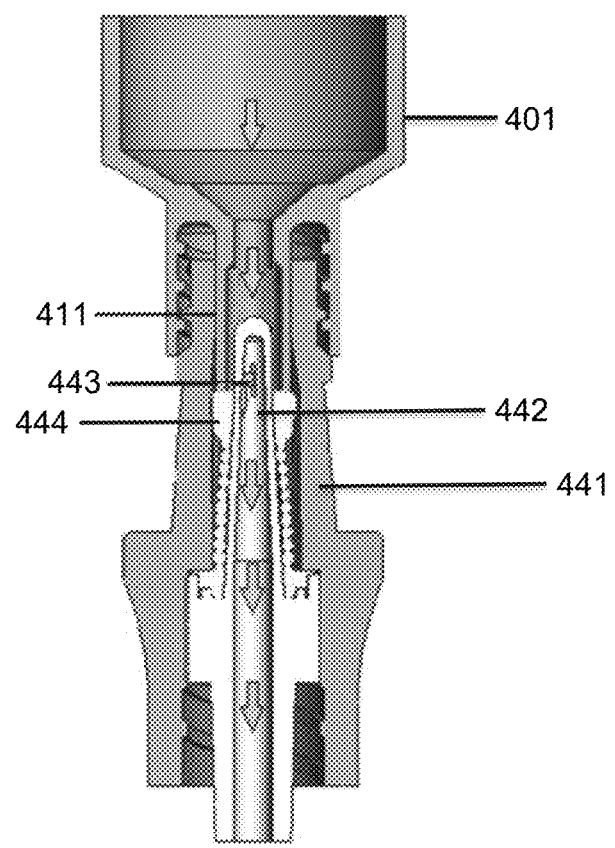
FIG. 4 depicts an exemplary connection between a syringe according to the inventive subject matter to a needleless connector with a reversed internal blunt cannula.
Figure 5A:
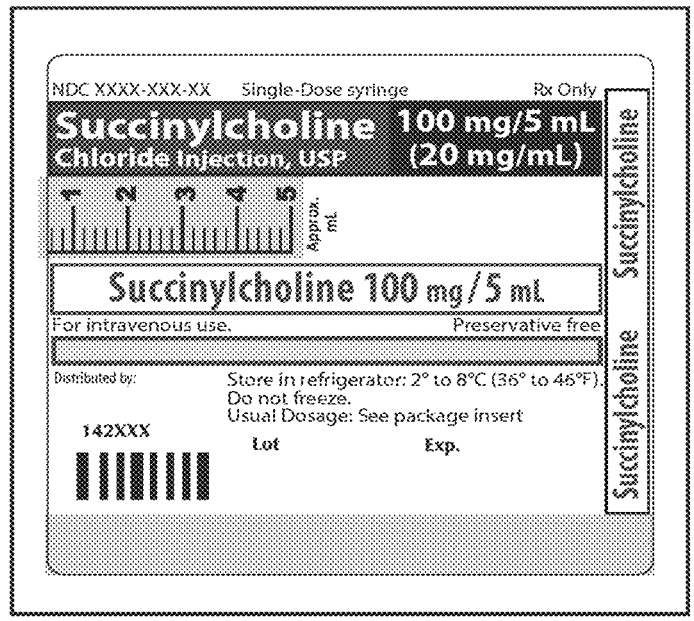
FIGS. 5A and 5B depict exemplary labels for prefilled syringes.
Figure 5B:
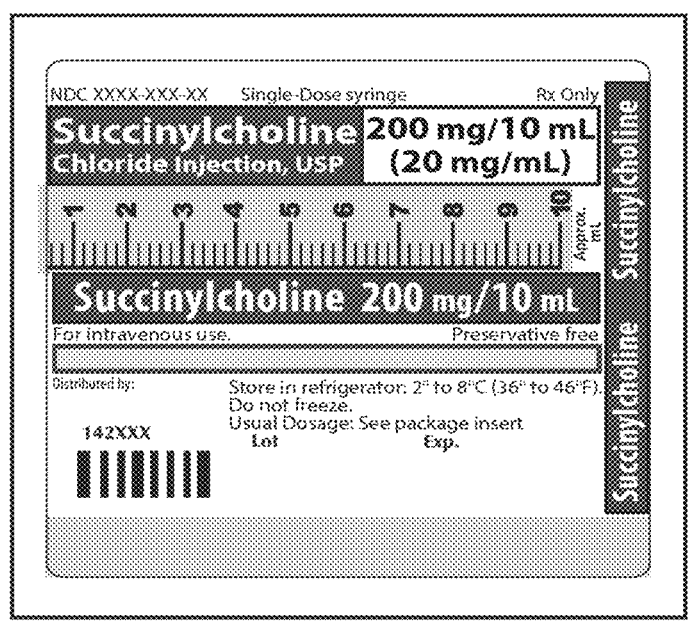

For example, FIG. 3 exemplarily depicts on the left hand a conventional syringe 300 that has a syringe tip 310 having an internal diameter 320 (here: 1.1 mm). The syringe also includes a luer lock connector 330 that is releasably coupled to matching luer lock of a needleless connector 340 (internals not shown) of an IV line. In contrast, on the right hand syringe 301 is shown having a syringe tip 311 with a significantly larger internal diameter 321 (here: 1.7 mm). The syringe also includes a luer lock connector 331 that is releasably coupled to matching luer lock of a needleless connector 341 (internals not shown) of an IV line. As should be readily apparent, the wider internal diameter accommodates angled insertion of the syringe tip 311 without jamming or breaking the internals (such as a reversed internal blunt cannula). FIG. 4 schematically illustrates one such embodiment in which syringe 401 has a syringe tip 411 with a significantly larger internal diameter. As can be seen, the reversed internal blunt cannula 442 of needleless connector 441 does not contact the internal walls of syringe tip 411. Instead, due to the wider inner diameter of the tip, an annular void space between the outer surface of the reversed internal blunt cannula and the internal walls of syringe tip is present that reduces or even entirely eliminates the risk of breakage or jamming of the front end of the reversed internal blunt cannula. FIGS. 5A and 5B depict exemplary labels for prefilled syringes according to the inventive subject matter.

Notably, despite the loss of a sealing surface (i.e., the outside surface of reversed internal blunt cannula against internal wall of the syringe tip) the connection between the syringe and the needleless connector nevertheless remained fluidly sealed by compression of elastic member 444 against the front end of the syringe tip and further by sealing engagement between the outer surface of the syringe tip 411 and the inner surface of the front portion of the connector that receives the syringe tip 411. Even at elevated pressure, these remaining surfaces maintained a fluid-tight contact that allowed rapid delivery of fluids through the connection.

Most preferably, the syringe for use in conjunction with the teachings herein may be a glass syringe (e.g., borosilicate glass), and in less preferred embodiments also a syringe manufactured from a polymeric material such as polypropylene or polyethylene. Moreover, it is preferred that the syringe has a volume of at least 5 mL or at least 10 mL, however, smaller volumes are also expressly contemplated. In one embodiment, the syringe has a volume of 5 mL. In another embodiment, the syringe has a volume of 10 mL. With respect to the tip it typically preferred that the tip is a centrally located tip, but eccentric tips are also deemed suitable. Most typically, the syringe tip will have an outer diameter, angle, and length that accommodate standard hub dimensions of luer lock needles and other luer lock equipment. Standards for luer lock connections are described in ISO 80369 and in DIN and EN standard 1707:1996 and 20594-1:1993, incorporated by reference herein.

For example, a typical tip of a syringe for luer-type connection will have a cone shaped configuration acting as the male portion of the luer lock with an overall length of about 7.5 mm from proximal to distal end (with respect to the barrel) of the tip, the proximal end of the tip having an outer diameter of about 4.45 mm and the distal end of the tip having an outer diameter of about 4.00 mm. Thus, a taper angle (relative to a hypothetical axis running through the center of the barrel and tip) of the tip walls between 0.5 degree and 5.0 degree are generally deemed suitable. However, the actual taper angle will in most cases correspond to the female luer lock counterpart such that the outer surface of the male and inner surface of the female connector will sealingly coupled the male and female portions (i.e., have the same angle along at least 70% of the length of the male tip).

With respect to the overall length of the tip as measured from proximal to distal end it is generally preferred that the length will be between about 8.5 mm to about 6.0 mm, however, various longer and shorter lengths are also deemed suitable for use herein. For example, suitable lengths include those between 5.5 mm and 7.0 mm, and between 6.0 mm and 8.0 mm, and between 7.0 mm and 9.0 mm. However, lengths of equal or less than 8.0 mm are generally preferred. With respect to the inner diameter of the tip it is generally preferred that the inner diameter is constant from the proximal to the distal end of the tip. Most typically the inner diameter will be about 1.7 mm, however various other inner diameters are also deemed suitable for use herein. For example, alternative inner diameters will generally be greater than 1.1 mm, or greater than 1.3 mm, or greater than 1.5 mm, or greater than 1.7 mm, or greater than 1.9 mm, or even greater. Thus, suitable inner diameters will be between 1.2-2.2 mm, or between 1.4-2.0 mm, or between 1.6-1.8 mm, or between 1.3-1.6 mm, or between 1.5-1.9 mm, or between 1.6-2.0 mm. Viewed from a different perspective, the inner diameter and/or the length of the tip will be selected such that the syringe and tip can be inserted into the needleless connector at an angle (with respect to a hypothetical central axis extending through the barrel and the tip of the syringe and a hypothetical central axis longitudinally extending through the needleless connector) without the reversed internal blunt cannula contacting the inner surface of the tip. In some embodiments, such angle will be 5 degrees, or 7 degrees, or 10 degrees, or 12.5 degrees, or 15 degrees, or 20 degrees, or even higher. While not limiting to the inventive subject matter, contemplated syringes may have a fixed or a rotating (typically polymeric) lock portion. Still further, it is contemplated that contemplated syringes will have a tip cap rubber surface contact area of equal or more than 2.4 mm$^2$, and more preferably equal or more than 4.8 mm$^2$. In still further contemplated embodiments, the syringe has a glide force of about 1 to about 30 N, about 1 to about 20N, or about 1 to about 10N. In other embodiments, the syringe has a break loose force of about 10 to about 30 N or about 15 to 25N. Exemplary syringes are commercially available, for example, from Becton Dickinson under the brand name Hylok or LLEC (Luer Lock extended channel), which are commonly used for viscous materials such as dermal fillers.

It should be recognized that the syringes contemplated herein will be particularly suitable for use with drug compositions that are administered in an emergency setting where administration must be performed promptly and without interruption necessitated by clearing a clogged line, reconnecting a malfunctioning syringe, and/or preparing a new vascular access. Typical drugs for use with the syringes presented herein include those used in cardiac/vascular emergencies, pulmonary emergencies, anaphylaxis, etc. Consequently, suitable drugs include succinylcholine, ephedrine, amiodarone, adenosine, epinephrine, atropine, methylprednisolone, metoprolol, diltiazem, and procainamide. In most embodiments, the syringes will be prefilled with a volume of the drug, typically at a volume of at least 1 mL, or at least 5 mL, or at least 10 mL, or about 5 mL or about 10 mL. As will be readily appreciated, the emergency drug in such products will be present at a pharmaceutically effective concentration to treat any emergency condition. Suitable formulation types of the drug compositions include solutions with single, binary, or higher solvent systems, dispersed systems (e.g., preferably emulsions or suspensions)

Of course, it should also be appreciated that the prefilled syringe may be provided with an IV administration set or other bags or tubing that will most typically comprise at least one needleless connector that may or may not have a reversed internal blunt cannula. Still further, it should be noted that the prefilled syringe will typically be sterilized using terminal sterilization, e-beam or gamma ray radiation, ethylene oxide, etc.

Moreover, it should be recognized that contemplated prefilled glass syringes are especially advantageous for drug compositions that are sensitive to components that would otherwise leach from a plastic syringe (such as plasticizers, dyes, metals, etc.), particularly where the pH of the drug composition is in the acidic range (e.g., equal or less than 5.0, or equal or less than 4.5, or equal or less than 4.0, or equal or less than 3.5), where the drug is sensitive to oxygen ingress, or where the composition comprises a solvent that is incompatible with polymers used in plastic syringes such as polypropylene or polyethylene. Therefore, and viewed form a different perspective, contemplated systems and methods will also advantageously help improve chemical stability of otherwise relatively labile compounds (e.g., succinylcholine) under refrigeration conditions (about 2° C. to about 8° C., or about 5° C.) and at room temperature (about 25° C.).

For example, the stability of a succinylcholine composition in a glass syringe will typically be increased such that total impurities are equal or less than 12%, or equal or less than 10%, more typically equal or less than 8%, even more typically equal or less than 6%, or equal or less than 4%, or equal or less than 2% after storage at 2-8° C. for 12, 15, 18, or 24 months as determined HPLC as is described in more detail below. Thus, total impurities will preferably be in the range of between 1-3%, or between 2-5%, or between 4-8%, or between 5-10% after storage at 2-8° C. for 15 months as determined HPLC. Additionally, it is contemplated that after storage of a succinylcholine composition in a glass syringe at 2-8° C. for 12, 15, 18, or 24 months, no more than 8%, or no more than 6%, or no more than 4%, or no more than 2% of succinylmonocholine chloride (as primary degradation product) are present. Thus, succinylmonocholine chloride may be present after storage of a succinylcholine composition in a glass syringe at 2-8° C. for 12, 15, 18, or 24 months in a range of between 1-3%, or between 2-5%, or between 4-8%, or between 5-10%.

In further contemplated aspects, improved stability is also contemplated where the succinylcholine composition is stored in a glass syringe at about 25° C. For example, succinylmonocholine chloride may be present after storage of a succinylcholine composition in a glass syringe at about 25° C. for 14-60 days (or for 7-14 days, or for 14-21 days, or for 21-28 days, or for 28-40 days, or for 40-60 days) in a range of between 1-3%, or between 2-5%, or between 4-8%, or between 5-10%, particularly where the prefilled syringe was not previously subjected extended storage at 2-8° C. In such cases, for example where the previous refrigerated storage was between 1-3 months, the succinylmonocholine chloride may be present after subsequent storage about 25° C. for 14-60 days (or for 7-14 days, or for 14-21 days, or for 21-28 days, or for 28-40 days, or for 40-60 days) in a range of between 2-5%, or between 4-8%, or between 5-10%. Likewise, where the previous refrigerated storage was between 3-6 months, the succinylmonocholine chloride may be present after subsequent storage about 25° C. for 14-50 days (or for 7-14 days, or for 14-21 days, or for 21-28 days, or for 28-40 days, or for 40-50 days) in a range of between 3-6%, or between 5-9%, or between 8-12%, and where the previous refrigerated storage was between 6-15 months, the succinylmonocholine chloride may be present after subsequent storage about 25° C. for 14-40 days (or for 7-14 days, or for 14-21 days, or for 21-28 days, or for 28-40 days) in a range of between 3-7%, or between 5-10%, or between 8-12%.

In some embodiments, the drug composition comprises a drug for emergency medical administration, a toncity agent, optionally one or more pH adjusting agents, and water.

In some embodiments, the drug for emergency medical administration is succinylcholine, selected from the group consisting of ephedrine, amiodarone, adenosine, epinephrine, atropine, methylprednisolone, metoprolol, diltiazem, and procainamide, and pharmaceutically acceptable salts thereof. In preferred embodiments, the drug for emergency medical administration is succinylcholine or a pharmaceutically acceptable salt thereof, and most preferably, succinylcholine chloride. In some embodiments, the drug for emergency medical administration is present in the composition in a therapeutically effective amount. In some embodiments, the drug for emergency medical administration is succinylcholine chloride and the succinylcholine chloride is present in the composition in an amount of about 10 to about 30 mg/mL, about 15 to about 25 mg/mL, or about 20 mg/mL.

In some embodiments, the tonicity agent is selected from the group consisting of dextrose, mannitol, potassium chloride, and sodium chloride. In preferred embodiments, the tonicity agent is sodium chloride. In some embodiments, the tonicity agent is present in the composition in an amount sufficient to provide an isotonic solution. In some embodiments, the tonicity agent is present in the composition in an amount sufficient to provide an osmolality of about 260 to about 340 mOsm/kg. In some embodiments, the tonicity agent is sodium chloride and the sodium chloride is present in the composition in an amount of about 4 to about 7 mg/mL, about 5 to about 6 mg/mL, about 5 mg/mL, or about 6 mg/mL.

In some embodiments, the pH adjusting agents are selected from the group consisting of acidifying agents, alkalizing agents, and buffering agents. In some embodiments, the pH adjusting agent is selected from the group consisting of citric acid, acetic acid, hydrochloric acid, sodium hydroxide, sodium citrate, potassium hydroxide, and potassium citrate. In preferred embodiments, pH adjusting agent is hydrochloric acid and/or sodium hydroxide. In some embodiments, the pH adjusting agent is present in the composition in an amount sufficient to provide a pH of about 3 to about 4.5, about 3 to about 4, about 3.5 to about 4.5, or about 3.5 to about 4, or about 3.6.

EXAMPLES

Example 1: Succinylcholine Composition

In one example, where the drug composition comprises succinylcholine, a 5 mL or 10 mL glass syringe (e.g., syringes with inner tip diameter of 1.7 mm) can be filled with a composition as shown in Table 1 where the composition has a pH of about 3.0 to about 4.5. Tonicity is adjusted to about 260 to about 340 mOsm/kg, and in preferred aspects, the succinylcholine chloride is present in the succinylcholine composition in an amount of about 20 mg/mL and the sodium chloride is present in the succinylcholine composition in an amount of about 5.50-6.00 mg/mL.

TABLE 1

| Ingredient | Grade | Function | Qty/mL |
|---|---|---|---|
| Succinylcholine Chloride | USP | Active ingredient | 20.0 mg |
| Sodium Chloride | USP | Tonicity agent | 5.56 mg |
| Hydrochloric Acid | NF | pH adjuster | q.s. for pH adjustment to about pH 3.6 |
| Sodium Hydroxide | NF | pH adjuster | q.s. for pH adjustment to about pH 3.6 |
| Water for Injection | USP | Vehicle | q.s. to 1.0 mL 5 ml per Syringe 10 ml per Syringe |

Example 2: Stability of a Succinylcholine Composition at 25° C.

Advantageously, thusly prefilled glass syringes afford relatively high stability and purity throughout extended periods of storage despite the acidic pH of the solution.

Three batches of the succinylcholine composition of Example 1 in a 5 mL Becton Dickinson LLEC glass syringe with inner tip diameter of 1.7 mm were prepared and stability was tested over 3 months of storage at 25° C. and 60% relative humidity. Content of succinylcholine chloride, impurities succinylmonocholine chloride, succinic acid, unidentified impurity 1, unidentified impurity 2, and total impurities were measured at 0, 1, 2, and 3 months by HPLC according to Example 4 below. Unidentified impurity 1 and unidentified impurity 2 are referenced in the USP monograph for impurity detection in succinylcholine, First Supplement to USP 39-NF 34. Appearance, pH, osmolality, and particulate content were also measured at 0, 1, 2, and 3 months. The results are included in Table 2 below.

TABLE 2

| Month | Batch | Appearance* | pH | SCC | SMCC | SA | Impurity 1 | Impurity 2 | Total impurities | P ≥ 10 μm | P ≥ 25 μm | Osmolality (mOsm/kg) |
|---|---|---|---|---|---|---|---|---|---|---|---|---|
| 0 | 1 | complies | 3.9 | 99.3% | 0.5% | <LOQ | <LOQ | <LOQ | 0.5% | 34 | 0 | 314 |
| 0 | 2 | complies | 3.9 | 99.8% | 0.4% | ND | 0.2% | <LOQ | 0.4% | 25 | 0 | 313 |
| 0 | 3 | complies | 3.9 | 97.6% | 0.4% | ND | <LOQ | 0.2% | 0.4% | 65 | 1 | 312 |
| 1 | 1 | complies | 3.4 | 93.5% | 2.5% | 0.1% | 0.2% | ND | 2.7% | — | — | — |
| 1 | 2 | complies | 3.4 | 94.8% | 2.3% | 0.1% | <LOQ | 0.1% | 2.4% | — | — | — |
| 1 | 3 | complies | 3.4 | 94.5% | 2.2% | 0.1% | <LOQ | <LOQ | 2.3% | — | — | — |
| 2 | 1 | complies | 3.3 | 93.8% | 4.0% | 0.3% | 0.5% | 0.1% | 4.3% | — | — | — |
| 2 | 2 | complies | 3.3 | 93.8% | 3.9% | 0.3% | 0.3% | 0.3% | 4.2% | — | — | — |
| 2 | 3 | complies | 3.3 | 93.8% | 3.8% | 0.2% | 0.3% | 0.3% | 4.0% | — | — | — |
| 3 | 1 | complies | 3.3 | 91.6% | 4.9% | 0.4% | 0.2% | <LOQ | 5.4% | 75 | 1 | 316 |
| 3 | 2 | complies | 3.3 | 92.7% | 4.9% | 0.4% | 0.1% | <LOQ | 5.3% | 63 | 0 | 318 |
| 3 | 3 | complies | 3.3 | 92.6% | 4.8% | 0.4% | 0.1% | <LOQ | 5.2% | 133 | 0 | 316 |

ND = not detected;
*Clear, colorless solution essentially free of visible particles;
SCC: Succinylcholine chloride;
SMCC: Succinylmonocholine chloride;
SA: Succinic acid;
P: Particle;
<LOQ = that the amount detected is less than the limit of quantitation of the HPLC method.
— = not measured.

As illustrated by Table 2 above, the succinylcholine composition in the glass syringe contained not more than about 6% total impurities after storage at 25° C. for 3 months as determined by HPLC. Likewise, with respect to degradation it was determined that the succinylcholine composition in the glass syringe contained not more than about 4% succinylmonocholine chloride (as primary degradation product) after storage at 25° C. for 3 months as determined by HPLC, and that the succinylcholine composition in the glass syringe contained not more than about 1% succinic acid after storage at 25° C. for 3 months as determined by HPLC.

Example 3: Stability of a Succinylcholine Composition at 5° C.

Stability of the three batches of Example 2 was also tested over 3 months of storage at 5° C. Content of succinylcholine chloride, impurities succinylmonocholine chloride, succinic acid, unidentified impurity 1, unidentified impurity 2, and total impurities were measured at 0 and 3 months by HPLC according to Example 4 below. Unidentified impurity 1 and unidentified impurity 2 are referenced in the USP monograph for impurity detection in succinylcholine, First Supplement to USP 39-NF 34. Appearance, pH, osmolality, and particulate content were also measured at 0 and 3 months. The results are included in Table 3 below.

TABLE 3

| Month | Batch | Appearance* | pH | SCC | SMCC | SA | Impurity 1 | Impurity 2 | Total impurities | P ≥ 10 µm | P ≥ 25 µm | Osmolality (mOsm/kg) |
|---|---|---|---|---|---|---|---|---|---|---|---|---|
| 0 | 1 | complies | 3.9 | 99.3% | 0.5% | <LOQ | <LOQ | <LOQ | 0.5% | 34 | 0 | 314 |
| 0 | 2 | complies | 3.9 | 99.8% | 0.4% | ND | 0.2% | <LOQ | 0.4% | 25 | 0 | 313 |
| 0 | 3 | complies | 3.9 | 97.6% | 0.4% | ND | <LOQ | 0.2% | 0.4% | 65 | 1 | 312 |
| 3 | 1 | complies | 3.7 | 98.3% | 1.1% | <LOQ | 0.2% | <LOQ | 1.1% | 66 | 0 | 310 |
| 3 | 2 | complies | 3.6 | 98.9% | 0.9% | <LOQ | 0.1% | <LOQ | 0.9% | 88 | 1 | 311 |
| 3 | 3 | complies | 3.7 | 99.3% | 0.9% | <LOQ | 0.1% | <LOQ | 0.9% | 63 | 0 | 310 |

ND = not detected;
*Clear, colorless solution essentially free of visible particles;
SCC: Succinylcholine chloride;
SMCC: Succinylmonocholine chloride;
SA: Succinic acid;
P: Particle;
<LOQ = that the amount detected is less than the limit of quantitation of the HPLC method.
— = not measured.

As illustrated by Table 3 above, the succinylcholine composition in the glass syringe contained not more than about 2% total impurities after storage at 5° C. for 3 months as determined by HPLC. Likewise, with respect to degradation it was determined that the succinylcholine composition in the glass syringe contained not more than about 2% succinylmonocholine chloride (as primary degradation product) after storage at 5° C. for 3 months as determined by HPLC, and that the succinylcholine composition in the glass syringe contained not more than about 1% succinic acid after storage at 5° C. for 3 months as determined by HPLC.

Example 4: Analytic Protocols

In general, analytic protocols for succinylcholine are well known in the art, and the following TLC and HPLC protocols are suitable for use herein (which are based on the USP monographs):

Analytic Protocol (TLC):
Standard solution: 1 mg/mL of USP Succinylcholine Chloride RS in water; Sample solution: 1 mg/mL of succinylcholine chloride in water; Adsorbent: 0.25-mm layer of chromatographic silica gel with an application volume of 1 mcL. The plate is run with a developing solvent system that consists of acetone and 1 N hydrochloric acid (1:1). Analysis is performed by running standard and sample solution in parallel. Sample and standard spots are detected by heating the plate to 105° C. for 5 min, followed by cooling and spraying with potassium bismuth iodide test solution and subsequent heating to 105° C. for another 5 min.

Analytic Protocol (HPLC) for Succinylcholine:
Mobile phase: Prepare a 1 in 10 solution of 1 N aqueous tetramethylammonium chloride in methanol. Adjust with hydrochloric acid to a pH of about 3.0.
Standard solution: 8.8 mg/mL of USP Succinylcholine. Succinylcholine Chloride Chloride RS prepared as follows. Transfer a suitable amount of USP Succinylcholine Chloride RS to a suitable volumetric flask and dissolve in 40% of the total volume of water. Dilute with Mobile phase to volume while mixing.
Sample solution: 8.8 mg/mL of Succinylcholine Chloride prepared as follows. Transfer a suitable amount of Succinylcholine Chloride to a suitable volumetric flask and dissolve in 40% of the total volume of water. Dilute with Mobile phase to volume while mixing.
Conventional HPLC system is operated using UV detection at 214 nm and a 4-mm×25-cm, 10 µm L3 packing (normal phase, silica) at a flow rate of 0.75 ml/min.

Analysis is performed on standard and sample solutions and percentage of succinylcholine chloride is calculated using the following equation: Result=$(r_U/r_S) \times (C_S/C_U) \times 100$, where $r_U$ is peak response from the sample solution, $r_S$ is peak response from the standard solution, $C_S$ is concentration of USP Succinylcholine Chloride RS in the standard solution (mg/mL), and $C_U$ is concentration of Succinylcholine Chloride in the sample solution (mg/mL).

Analytic Protocol (HPLC) for Impurities:
Buffer: 3.85 g/L of anhydrous sodium 1-pentanesulfonate, 2.9 g/L of sodium chloride, and 1% (v/v) of 1 N sulfuric acid in water.
Mobile phase: Acetonitrile and Buffer (5:95).
Standard solution: 0.05 mg/mL of USP Succinylmonocholine Chloride RS in Mobile phase.
Sample solution: Sample solution: 10 mg/mL of Succinylcholine Chloride in mobile phase.
Conventional HPLC system is operated using UV detection at 214 nm and a 4.6-mm×25-cm, L1 packing (octadecyl silane chemically bonded to porous silica or ceramic microparticles, 1.5 to 10 µm in diameter) at a flow rate of 0.75 ml/min.

Analysis is performed on standard and sample solutions and percentage of succinylcholine chloride is calculated using the following equation: Result=$(r_U/r_S) \times (C_S/C_U) \times (1/F) \times 100$, where $r_U$ is peak response from the sample solution, $r_S$ is peak response from the standard solution, $C_S$ is concentration of USP Succinylcholine Chloride RS in the standard solution (mg/mL), $C_U$ is concentration of Succinylcholine Chloride in the sample solution (mg/mL), and F is the relative response factor.

Example 5: Syringe Parameters

Break loose force and glide force were also measured in quintuplicate at each time point in Examples 2 and 3 above. The results are included in Table 4 below:

TABLE 4

| Month | Temperature | Batch | Break Loose Force (Newtons) | Glide Force (Newtons) |
|---|---|---|---|---|
| 0 | 25° C. | 1 | 16, 16, 16, 16, 13 | 6, 24, 6, 20, 5 |
| 0 | 25° C. | 2 | 13, 16, 14, 18, 15 | 5, 11, 6, 7, 11 |
| 0 | 25° C. | 3 | 16, 14, 18, 18, 24 | 14, 13, 9, 6, 7 |
| 1 | 25° C. | 1 | 16, 19, 21, 18, 16 | 6, 6, 21, 17, 12 |
| 1 | 25° C. | 2 | 19, 17, 13, 16, 17 | 28, 6, 8, 9, 6 |
| 1 | 25° C. | 3 | 18, 21, 15, 15, 21 | 8, 23, 16, 12, 7 |
| 2 | 25° C. | 1 | 20, 18, 19, 17, 22 | 5, 6, 7, 4, 6 |

TABLE 4-continued

| Month | Temperature | Batch | Break Loose Force (Newtons) | Glide Force (Newtons) |
|---|---|---|---|---|
| 2 | 25° C. | 2 | 23, 19, 16, 19, 17 | 5, 10, 6, 5, 6 |
| 2 | 25° C. | 3 | 16, 18, 16, 21, 21 | 9, 6, 8, 11, 10 |
| 3 | 25° C. | 1 | 22, 19, 19, 19, 18 | 9, 12, 8, 8, 6, 9 |
| 3 | 25° C. | 2 | 15, 19, 18, 22, 19 | 6, 7, 16, 13, 8 |
| 3 | 25° C. | 3 | 25, 25, 22, 14, 17 | 6, 9, 6, 6, 6 |
| 3 | 5° C. | 1 | 23, 16, 19, 20, 18 | 23, 7, 6, 33, 7 |
| 3 | 5° C. | 2 | 20, 17, 20, 22, 10 | 9, 6, 18, 7, 6 |
| 3 | 5° C. | 3 | 15, 17, 18, 16, 20 | 9, 26, 6, 7, 8 |

As used herein, the term "administering" a pharmaceutical composition or drug refers to both direct and indirect administration of the pharmaceutical composition or drug, wherein direct administration of the pharmaceutical composition or drug is typically performed by a health care professional (e.g., physician, nurse, etc.), and wherein indirect administration includes a step of providing or making available the pharmaceutical composition or drug to the health care professional for direct administration (e.g., via injection, infusion, oral delivery, topical delivery, etc.).

In some embodiments, the drug composition in the prefilled syringe is administered to a patient via the patient's intravenous line. In some embodiments, the drug composition in the prefilled syringe is administered to the patient by reversibly attaching the syringe to the patient's intravenous line via the Luer-lock, delivering the drug composition from the syringe into the patient's intravenous line, and administering the drug composition from the patient's intravenous line to the patient. The succinylcholine drug composition is typically administered to the patient at a rate sufficient to cause the desired skeletal muscle relaxation. In some embodiments, the succinylcholine drug composition is administered to the patient at a rate of about 0.5 to about 10 mg per minute or about 2 to about 5 mg per minute, or about 2.5 to about 4.3 mg per minute. In some embodiments, the succinylcholine drug composition is administered to the patient in an amount of about 0.01 to about 3 mg/kg, about 0.04 to about 0.07 mg/kg, about 0.3 to about 1.1 mg/kg, about 0.6 mg/kg, 1 mg/kg, or 2 mg/kg.

In some embodiments, the present invention encompasses a method for providing skeletal relaxation comprising administering the succinylcholine drug composition in a prefilled syringe to a patient in need thereof via the patient's intravenous line. In some embodiments, the succinylcholine drug composition is administered as an adjunct to general anesthesia, to facilitate tracheal intubation, or to provide skeletal muscle relaxation during surgery or mechanical ventilation.

The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided with respect to certain embodiments herein is intended merely to better illuminate the full scope of the present disclosure, and does not pose a limitation on the scope of the invention otherwise claimed. The term "about" where used in conjunction of a numeric value refers to a range of +/−10% of that numeric value, inclusive. No language in the specification should be construed as indicating any non-claimed element essential to the practice of the claimed invention.

It should be apparent to those skilled in the art that many more modifications besides those already described are possible without departing from the full scope of the concepts disclosed herein. The disclosed subject matter, therefore, is not to be restricted except in the scope of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:

1. A method for intravenously administering succinylcholine to a patient in need thereof, comprising:
   (a) providing a prefilled glass syringe containing a succinylcholine composition, wherein the succinylcholine composition has a pH of about 3.0 to about 4.5, wherein the succinylcholine composition disposed in the glass syringe contains not more than about 6% total impurities after storage at 2-8° C. for 12 months, followed by storage at about 25° C. for 14 days as determined by HPLC, and wherein the syringe has a Luer-lock and a syringe tip with an internal channel that has a diameter of about 1.7 mm;
   (b) reversibly attaching the syringe to a patient's intravenous line via the Luer-lock;
   (c) delivering the succinylcholine composition from the syringe into the patient's intravenous line; and
   (d) administering the succinylcholine composition from the patient's intravenous line to the patient.

2. The method of claim 1, wherein the step of reversibly attaching the syringe to a patient's intravenous line comprises attaching the syringe to a needleless connector.

3. The method of claim 2 wherein the needleless connector has a reversed internal blunt cannula.

4. The method of claim 1, wherein the glass syringe has a volume of at least 5 mL.

5. The method of claim 1, wherein the succinylcholine composition has an osmolality of about 260 to about 340 mOsm/kg.

6. The method of claim 1, wherein the succinylcholine chloride is present in the succinylcholine composition in an amount of about 20 mg/mL and sodium chloride is present in the succinylcholine composition in an amount of about 6 mg/mL.

7. The method of claim 1, wherein the succinylcholine composition further comprises a pH adjusting agent.

8. The method of claim 7, wherein the pH adjusting agent is hydrochloride acid and/or sodium hydroxide.

9. The method of claim 1, wherein the pH of the succinylcholine composition is about 3.6.

10. The method of claim 1, wherein the syringe has a glide force of about 1 to about 20 N.

11. The method of claim 1, wherein the syringe has a break loose force of about 10 to about 30 N.

12. The method of claim 1, wherein the succinylcholine composition is administered to the patient at a rate of about 0.5 to about 10 mg per minute.

13. The method of claim 1, wherein the syringe contains about 5 mL of the succinylcholine composition, or wherein the syringe contains about 10 mL of the succinylcholine composition.

14. The method of claim 1, wherein the succinylcholine composition comprises succinylcholine chloride, sodium chloride, and water, wherein the succinylcholine composition is substantially free of preservatives.

15. The method of claim 1, wherein the succinylcholine composition disposed in the glass syringe contains not more than about 6% total impurities and no more than 4% succinylmonocholine chloride after storage at 2-8° C. for 12 months, followed by storage at about 25° C. for 14 days, as determined by HPLC.

16. The method of claim 1, wherein the succinylcholine composition disposed in the glass syringe contains not more than about 4% total impurities not more than about 4% succinylmonocholine chloride after storage at 2-8° C. for 12 months, followed by storage at about 25° C. for 14 days, as determined by HPLC.

17. The method of claim 1, wherein the succinylcholine composition disposed in the glass syringe contains not more than about 1% succinic acid after storage at 2-8° C. for 12 months, followed by storage at about 25° C. for 14 days, as determined by HPLC.

18. A method for providing skeletal muscle relaxation to a patient in need thereof, comprising:
   a) providing a prefilled glass syringe containing a succinylcholine composition, wherein the succinylcholine composition has a pH of about 3.0 to about 4.5, wherein the succinylcholine composition disposed in the glass syringe contains not more than about 6% total impurities after storage at 2-8° C. for 12 months, followed by storage at about 25° C. for 14 days, as determined by HPLC, and wherein the syringe has a Luer-lock and a syringe tip with an internal channel that has a diameter of about 1.7 mm;
   b) reversibly attaching the syringe to a patient's intravenous line via the Luer-lock;
   c) delivering the succinylcholine composition from the syringe into the patient's intravenous line; and
   d) administering the succinylcholine composition from the patient's intravenous line to the patient.

19. The method of claim 18, wherein the step of reversibly attaching the syringe to a patient's intravenous line comprises attaching the syringe to a needleless connector that has a reversed internal blunt cannula, and optionally wherein the succinylcholine composition comprises succinylcholine chloride, sodium chloride, and water, wherein the succinylcholine composition is substantially free of preservatives.

* * * * *